(12) United States Patent
Martinez Openiano

(10) Patent No.: US 11,696,971 B1
(45) Date of Patent: Jul. 11, 2023

(54) PLURALITY OF DUAL UV-C LAMP SYSTEMS WIRELESSLY-REMOTELY-SIMULTANEOUSLY ACTIVATED/DEACTIVATED FROM A DISTANT CENTRAL LOCATION

(71) Applicant: Renato Martinez Openiano, Chula Vista, CA (US)

(72) Inventor: Renato Martinez Openiano, Chula Vista, CA (US)

( * ) Notice: Subject to any disclaimer, the term of this patent is extended or adjusted under 35 U.S.C. 154(b) by 0 days.

(21) Appl. No.: 18/090,478

(22) Filed: Dec. 28, 2022

Related U.S. Application Data

(60) Provisional application No. 63/361,576, filed on Dec. 31, 2021.

(51) Int. Cl.
| | |
|---|---|
| *H05B 47/115* | (2020.01) |
| *A61L 9/20* | (2006.01) |
| *H05B 47/155* | (2020.01) |
| *H05B 47/165* | (2020.01) |
| *H05B 47/16* | (2020.01) |

(52) U.S. Cl.
CPC .............. *A61L 9/20* (2013.01); *H05B 47/115* (2020.01); *H05B 47/155* (2020.01); *H05B 47/16* (2020.01); *H05B 47/165* (2020.01)

(58) Field of Classification Search
CPC ........ H05B 45/10; H05B 47/10; H05B 47/11; H05B 47/115; H05B 47/155; H05B 47/16; H05B 47/165; A61L 9/20
See application file for complete search history.

(56) References Cited

U.S. PATENT DOCUMENTS

| | | | |
|---|---|---|---|
| 2020/0289686 A1* | 9/2020 | Janik | G01V 11/002 |
| 2022/0001062 A1* | 1/2022 | Le | A61L 9/20 |

* cited by examiner

*Primary Examiner* — Jimmy T Vu
(74) *Attorney, Agent, or Firm* — Michael D. Eisenberg

(57) ABSTRACT

Embodiments of the present disclosure include a method for destroying pathogens in irradiating a region at a radiation having a wavelength between 200-300 nm via one or more lamps operatively connected to a respective cavity in responsive to processing a sequence associated with an inputted address. Embodiments also include controlling an operating status of the one or more lamps via a control center by sending a first command and sending a second command. Embodiments also include determining: a time frame of when the one or more lamps irradiate the region; and determining if there may be a motion.

20 Claims, 7 Drawing Sheets

Triac Control Switch of the FAR UVC Light as the Load Using Output from the CPU connected to Pin 2 of M0C34043M Optoisolator

| SUMMARY OF ECRC OVERALL COMPLIANCE | | | |
|---|---|---|---|
| | | Yes | No |
| ECRC No.: | 524123385 | | No |

| | | Operational Compliance | |
|---|---|---|---|
| | | Yes | No |
| IAPED No. | RO-1446542310 | | No |
| | AS-7447364403 | Yes | |
| | AD-6457263418 | Yes | |
| | MN-6569446932 | Yes | |
| | LM-0771885296 | Yes | |
| | SN-1139324862 | Yes | |
| | RO-0870355769 | Yes | |
| | NN-0789653228 | Yes | |
| | LL-1185780421 | Yes | |
| | YS-6644583960 | Yes | |

| | | Maintenance Compliance | |
|---|---|---|---|
| | | Yes | No |
| IAPED No. | RO-1446542310 | Yes | |
| | AS-7447364403 | Yes | |
| | AD-6457263418 | Yes | |
| | MN-6569446932 | Yes | |
| | LM-0771885296 | Yes | |
| | SN-1139324862 | Yes | |
| | RO-0870355769 | Yes | |
| | NN-0789653228 | Yes | |
| | LL-1185780421 | Yes | |
| | YS-6644583960 | Yes | |

FIG. 8

PLURALITY OF DUAL UV-C LAMP SYSTEMS WIRELESSLY-REMOTELY-SIMULTANEOUSLY ACTIVATED/DEACTIVATED FROM A DISTANT CENTRAL LOCATION

CROSS-REFERENCES TO RELATED APPLICATIONS

This application claims priority from U.S. Provisional Application Ser. No. 63/361,576 filed on Dec. 31, 2021 and entitled "Plurality of Dual UV-C Lamp Systems Wirelessly-Remotely-Activated/Deactivated From a Distant Central Location", which is hereby incorporated herein by reference in its entirety.

FIELD OF THE INVENTION

The present invention relates to systems and methods for creating and/or maintaining indoor environments devoid of pathogens.

BACKGROUND OF THE INVENTION

Pathogens, airborne and non-airborne, can lead to public health hardships, such as COVID-19. Currently, there is no Anti-COVID measure that guarantees 100% compliance. The subject of this invention is an Anti-COVID measure that guarantees 100% compliance whereby all of the devices of the invention installed nationwide can be simultaneously wirelessly, universally controlled remotely by the Master Communications Control Center (MCCC) operated by a controlling body, such as, for example, governmental or semi-governmental agency and/or their authorized representative, wherein the MCCC transmits the controlling command simultaneously to "all" the installed individual devices nationwide. The systems and methods herein address this technical problem whereby a far distant control center (e.g., MCCC) utilizes a non-transitory telecommunication signal capable of simultaneously transmitting the controlling command to "all" these installed pathogen eradicating devices of the invention (IAPED) nationwide via the multiplicity of establishments' communications relay center (ECRC) located in or near the vicinity of these establishments having the IAPED devices. In the systems and methods herein, MCCC can have authorizations which the owners/management/administrators of the public and private facilities/establishments where these devices are physically installed cannot override (i.e., cannot oppose/intervene) the authorizations of the MCCC to the turning on and off of these installed devices in their facilities/establishments).

BRIEF DESCRIPTION OF THE FIGURES

FIG. 8 is an example of data summaries collected by a relay center in telecommunication contact with the main controlled center and controlled irradiation systems.

BRIEF SUMMARY OF THE EMBODIMENTS OF THE INVENTION

Figure 1:
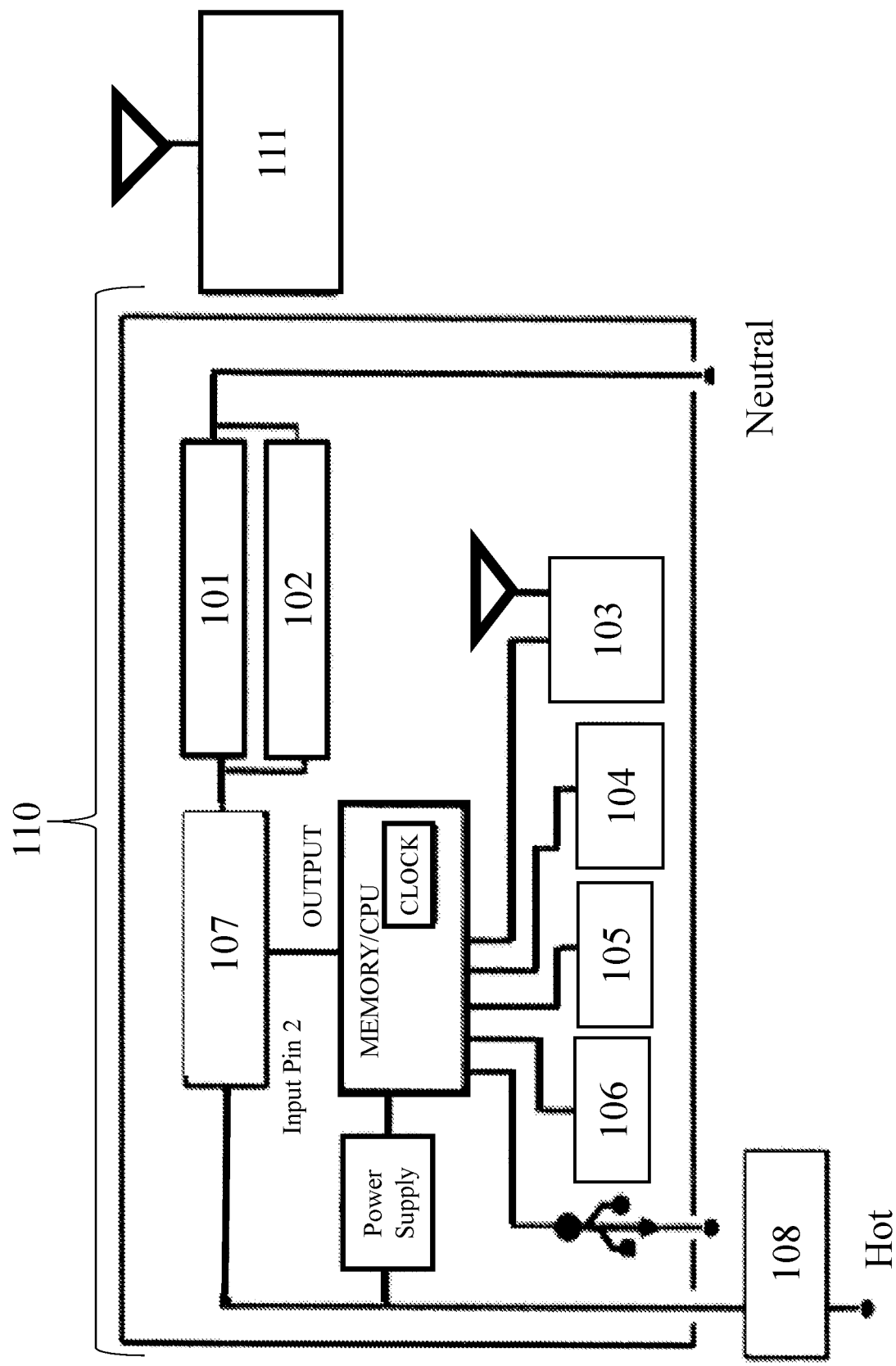
FIG. 1 and FIG. 2 are circuit diagrams of the controlled irradiation system and main control center.

In a variant, a method for destroying pathogens includes: universally wirelessly, simultaneously, and indiscriminately controlling an operating status of each pathogen lamp of a plurality of pathogen lamp installed within a respective cavity of a housing system of one or more housing systems, inside each participating establishments, facilities, buildings throughout the vast geographical region of a country within a cluster, by transmission of one or more non-transitory signals from a control center that simultaneously control the plurality of pathogen lamp in the cluster by: sending a first command; sending a second command; sending a subsequent command after the first command and the second command for determining a time frame of when the one or more lamps irradiate the region; determining if there is a motion; and processing a sequence associated with (i) an inputted address, (ii) days of office hours, or (iii) the inputted address and the days of office hours; and irradiating one or more regions within the cluster at a radiation having a wavelength between 200-300 nm via one or more pathogen lamps of the plurality of pathogen lamps operatively connected to a respective cavity, in response to transmitting at least one or more of the non-transitory signals as a command signal for controlling the operating status, based on the processed sequence associated with the inputted address, the days of office, or the input address and the days of the office hours and if the motion is determined.

In a variant, the operating status is a first state, a second state, or a third state.

In a variant, the first state is on, the second state is off, and the third state is standby.

In a variant, the first command and the second command is an on signal or an off signal.

In a variant, the first command is an off signal and the second command is an off signal, thereby putting each lamp is in a second state.

In a variant, the first command is an on signal and the second command is an on signal, thereby putting each lamp is in a first state.

In a variant, the first command is an on signal and the second command is an off signal, thereby putting each lamp is in a second state.

In a variant, the first command is an off signal and the second command is an on signal, thereby putting each lamp is in a first state.

In a variant, the method also includes an algorithm, as implemented by the control center, wherein the algorithm is: (1) automating an assessment of performance of the plurality of pathogen lamps by (2) deciding whether to activate a first, second, or third states, and wherein the control center overrides a management entity in the cluster.

In a variant, the method also includes using motion detectors to determine the operating status of each lamp.

In a variant, the method also includes transmitting periodic non-transitory signals associated with a first state, thereby activating the lamps within the one or more housing systems, and transmitting a subsequent non-transitory signal associated with a first state from the command center.

In a variant, transmitting the subsequent signal associated with the first state is spaced at one hour apart.

In a variant, transmitting the one or more non-transitory signals also includes transmitting the one or more non-transitory signals from the control center to a relay center, wherein the relay center processes the one or more non-transitory signals for transmission to the one or more housing systems, thereby controlling the operating status of each pathogen lamp of a plurality of pathogen lamp.

In a variant, the relay center determines if each housing system of the one or more housing systems is in a fourth state or a fifth state to apply a policy over the one or more housing systems.

In a variant, the fourth state is associated with an operationally compliant status and the fifth state is associated with an operationally non-compliant status.

In a variant, a computer system for destroying pathogens includes: a command center telecommunicatively connected with one or more housing systems within a cluster; a plurality of pathogen lamp operatively connected within the one or more housing units, wherein each housing system of the one or more housing systems contains one or two cavities, wherein the one or two cavities are configured to receive a respective pathogen lamp unit; wherein the command center transmits one or more non-transitory signals from a control center that simultaneously control the plurality of pathogen lamps in the cluster for: sending a first command; sending a second command; sending a subsequent command after the first command and the second command for determining a time frame of when the one or more lamps irradiate the region; determining if there is a motion; and processing a sequence associated with (i) an inputted address, (ii) days of office hours, or (iii) the inputted address and the days of office hours; and irradiating one or more regions within the cluster at a radiation having a wavelength between 200-300 nm from one or more pathogen lamps of the plurality of pathogen lamps operatively connected to a respective cavity, in response to transmitting at least one or more of the non-transitory signals as a command signal for controlling the operating status, based on the processed sequence associated with the inputted address, the days of office hours, or the input address and the days of the office hours, and if the motion is determined.

In a variant, the system also includes a relay center, wherein the relay center is operatively connected to the command center and the one or more housing systems within the cluster.

In a variant, the system also includes determining if each housing system of the one or more housing systems is in an operationally compliant status or an operationally non-compliant status to apply a policy over the one or more housing systems.

In a variant, the operating status is a first state, a second state, or a third state.

In a variant, the first state is on, the second state is off, and the third state is standby.

DETAILED DESCRIPTION OF THE EMBODIMENTS OF THE INVENTION

The system and methods herein pertain to a rigidly installed and/or hanging overhead UV-C Lamp device most preferably having a FAR 222 UV-C lamp (i.e., lamps 101 or 102) that is remotely/wirelessly turned "on" and "off" states by a far distant central control center, such as the Center for Disease Control (CDC), as main control center 201. Cluster 205 contains facility units whereby the lamps, as contained within controlled irradiation system 110, are located, wherein controlled irradiation system 110 is a dual lamp housing module. In cluster 205, once turned in an "on" state, these lamps (i.e., lamps 101 and 102 in controlled irradiation system 110) are continuously lit or operational (i.e., irradiate UV-radiation emitted from the lamps 101 and 102 in controlled irradiation system 110) during designated office hours of the controlled irradiation system 110. After these office hours, lamps 101 and 102 are continuously lit or operate for about 10 minutes per motion sensed by motion sensor 104.

To monitor strict operational and proper maintenance compliance by all the devices in cluster 205, each of these ECRCs (i.e., relay center 203) wirelessly communicate with each of the IAPED devices (i.e., controlled irradiation system 110) inside their respective establishments (cluster 205) to regularly collect operational and maintenance data from each of these IAPED devices. These ECRCs regularly transmits a summary of these collected data to the MCCC. If there are any indications of, for example, an ECRC is not transmitting any message; or any or all of the IAPED devices in any establishment has no electrical power, among many others from the collected data from any establishment, then main control center 201 can immediately contact the registered management/administrator of the establishments in cluster 205 via email, or other means to have the discrepancy corrected or face penalty and/or fine. In the event of further non-compliance, drastic measures such as suspending the business license to operate can be imposed against the management or administrator. The first initial exact time to turn to an "on" state of the IAPED after the first turn "on" state signal is received by the IAPED, as determined by a built-in algorithm using inputted street address of the establishment where these controlled lamps are installed, as described below; or the first initial exact time to turn to an "off" state of the IAPED after the first turn "off" signal is received by the IAPED is determined by the built-in algorithm using inputted street address of the establishment where these controlled lamps are installed.

The built-in algorithm can make determinations directly from main control center 201 or indirectly by instructing relay center 203 to assess operational compliance of each unit of an IAPED device (i.e., controlled irradiation system 110) of a plurality of IAPED devices in cluster 205, wherein the operational compliance is "Yes" or "No", whereby: (1) a "YES" for each unit of the IAPED device of the plurality of IAPED devices can, for example, allow for an "on" state signal to turn and/or keeps lamps 101 and 102 in an "on" state"; or (2) "NO" by at least a single unit of the IAPED device of the plurality of IAPED devices can, for example, ensure an "off" state signal to keep lamps 101 and 102 in an "off" state. Stated another way, a protocol is being enforced over each unit of an IAPED device (i.e., controlled irradiation system 110) of a plurality of IAPED devices in cluster 205, which in turn controls the operating state of the lamps (lamps 101 and 102) in controlled irradiation system 110.

Main control center 201 controls and implements the built-in algorithm for controlling the operating status of lamp units (i.e., lamps 101 and 102) within IAPED devices (i.e., controlled irradiation system 110) directly or indirectly through ECRCs (i.e., relay center 203), wherein the ECRC processes non-transitory signals from main control center 201 and transmits processed said non-transitory signals to IAPED devices (i.e., controlled irradiation system 110). For example, main control center 201 can send a Master Command Communications Center's (MCCC) operational command simultaneously transmitted to all of the country's plurality of establishments' Communications Relay Center (ECRC) within a transmission range, whereas these ECRCs can wirelessly relay the received operational command signal from the MCCC to all of respective IAPED devices inside their respective establishments in cluster 205, whereby all the ECRC units regularly collect operational and maintenance data from each of these IAPED devices in their establishment and these ECRCs regularly transmits a summary of these collected data to the MCCC (i.e., main control center 201), wherein each of these ECRC wirelessly communicates with each of the IAPED devices inside their respective establishments to regularly collect operational and maintenance data from each of these IAPED devices and these ECRCs regularly transmits a summary of these collected data to the MCCC (i.e., main control center 201).

A data summary is depicted in FIG. 8. In this depiction, the data summary pertains to a unit of relay center 203, which is ECRC No. 524123365 in this particular example. The built-in algorithm determines the unit of relay unit 203 reports an overall compliance of "NO" by virtue of a unit of controlled irradiation system 110, which is IAPED No. RO-1446542310, among a plurality of units of controlled irradiation system 110, reports an operational compliance of "NO". The first UV-C lamp in this IAPED is not turning "On". Stated another way, the built-in algorithm does not apply a majority or substantial majority of operational compliance type of determination in the protocol implemented within each unit of controlled irradiation system 110. Notice that this IAPED reported a "YES" in "Maintenance Compliance". Although 9 of the 10 IAPEDs have an operational compliance of "YES" in "Maintenance Compliance", this ECRC still reports a "No" simply by virtue of one of the 10 IAPEDs being non-compliant (i.e., an operational compliance of "No"). By virtue of ECRC has a "No" overall compliance, master control center 201 immediately contacts the manager/administrator of the facility/establishment within cluster 205 to inform them of this discrepancy and that this needs to be resolved. And any continued non-compliance is subject to fine and even revocation of their business permit to operate.

Main control center 201 can receive, at a prescribed interval from all the ECRCs, a summary of collected data comprising the operational and maintenance data from each of these IAPED devices in their respective establishments within cluster 205. If main control center 201 determines using an algorithm software that there are any indications of non-compliance from the collected data by any establishment, such as an ECRC is not transmitting any message or any or all of the IAPED devices has no electrical power, among others, main control center 201 can immediately and automatically contacts the registered management/administrator of the establishment via email, or other means to have the discrepancy corrected or face penalty and/or fine. In the event of further non-compliance, drastic measures such as the cancellation of their business permit to operate can be imposed against the management/administrator of the establishment.

The individual installed assembly of pathogen eradicating devices of the systems and methods herein, i.e., IAPED (controlled irradiation system 110) can be comprised of a housing structure having two cavities that each cavity can fittingly accommodate one properly fitted pathogen eradicating UV-C lamp (PEUVCL) or similar device, whereby these cavities can be physically oriented to allow an easy snap on installation of these PEUVCL into these cavities to facilitate easy removal and replacement of the PEUVCL into the cavities of the housing of this PEUVCL. without having to physically remove this housing from an installed position, wherein the IAPED is further comprised of one PEUVCL that is fittingly installed in one of the two cavities, and a second of the two cavities that is designed to fittingly accommodate an additional possible more potent PEUVCL or other applicable pathogen eradicating device should one be developed in the future.

The systems and methods herein use one built-in UV-Clamp (i.e., lamp 101) contained within a first cavity with a second built-in cavity that can accommodate a second UV-C Lamp (i.e., lamp 102). A different type of lamp 102, if found at a later date to help the lamp 101 eradicate more virus and bacteria or perhaps a newer variant, wherein lamp 101 is a filtered FAR UV-C Excimer Lamp Module, as used in Care 222® Filtered Krypton-Chloride 222 nm technology (Care 222) and manufactured by USHIO America as the first of two corona virus/bacteria killing lamps incorporated in controlled irradiation system 110. The reserved slot for this second UV-C lamp of different wavelength, i.e., lamp 102, that is as safe to humans indoor as Care 222, can augment to the effectiveness in killing newer variants that may come along. Existing lamps may be only be (1) effective at killing prior variants; or (2) effective at killing pathogens via high energy radiation (<400 nm), while also penetrating human skin or damaging eyes.

The enhanced effect comprises:
within controlled irradiation system 110, lamps 101 and 102 forming a filtering setup which: (a) captures high energy radiation (200-500 nm)), while (b) transmitting only radiation between 217-222 nm, thereby killing pathogens, without impacting humans or other species; and (c) transmits less heat per bulb over time;
configuring controlled irradiation system 110, which is telecommunication contact with main control center 201 or main control center 201 and relay center 203, as a facile, modulable system to control external lamps, wherein the external lamps are not integrated into controlled irradiation system 110, but electrically wired to controlled irradiation system 110, whereby an elongated UV-C lamps are transversely installed inside of airducts along the air flow path, thereby ensuring these lamps, when lit, are shining on the air entering airducts, wherein the airducts that supply indoor air to all these facilities/establishments have these external lamps strategically installed.

Stated another way, controlled irradiation system 110 can also be used to supply electrical power to preferably elongated UV-C lamps (not necessarily 222 nm), which are preferably installed in a matter that transverse in the middle portion inside the airduct.

By virtue of the systems and methods herein configured/designed to be a permanent fixture in the nation's effort to mitigate the spread of virus and bacteria, most notably COVID-19 and its variants as well as the common flu virus and other bacteria, leads to the advantageous effect of that there is no need to bring down this lamp system from the currently installed location of the lamp just to install this second UV-C lamp. More particularly in the systems and methods herein, there is an available second cavity specifically designed to accommodate lamp 102 as the second UV-C lamp that is designed to easily snap inside this cavity, which can augment the capability of lamp 101 should the need to add arise in the future years to come. This cavity for lamp 102, if not used, is covered by a removable cover for aesthetic purpose. Additionally, lamp 101 as the first UV-C lamp (Care 222), if needing a replacement in case of defect, can also easily be removed from respective cavity thereof (i.e., the first cavity of two cavities) without the following:

(1) having to bring down this lamp system from the currently installed location of the lamp; and (2) having to remove the unit and disassemble it.

Controlled Irradiation system 110 of the systems and methods is configured/designed to be remotely and wirelessly activated/deactivated from a far distance (but within the transmission range) by main control center 201, wherein main control center 201 is operated by a central governmental authority such as the Center for Disease Control and/or designated authorized representative. If main control center 201 is in the U.S. ("CDC"), then a central control location's Digital Cellular Network (DCN) using 4G-LTE, 4G, 5G, or any wireless data transmission means (WDT) preferably under the Internet of Things (IOT) frameworks are utilized, which can transmit non-transitory signals directly to relay point 203 or cluster 205, wherein cluster 205 contains facility units, wherein each facility unit is equipped with one or more units controlled irradiation system 110. Signal transmitter 111, which resides in main control center 201, can: (1) directly transmit said non-transitory signals to each unit of signal receiver 103 of each respective unit of controlled irradiation system 110 in cluster 205; or (2) directly transmits a non-transitory signal to relay center 203, wherein relay center 203 transmits a non-transitory signal to each unit of signal receiver 103 of each respective unit of controlled irradiation system 110.

In the event of any eminent or predicted threat of any such corona virus or any of its variants reaching the nation, even the flu virus or bacteria, the turn "on" state/activation signal can be sent remotely from main control center 201, thereby placing these plurality of UV-C Lamps (lamps 101 and 102) of the systems and methods herein in an "on" state, if within the selected office hours. If outside the office hours, lamps 101 and 102 can be turned to an "on" state when motion sensor activated via motion sensor 104, within the signal emission range of main control center 201, such as the CDC Control Center's range, to each of the respective units of controlled irradiation system 110 in cluster 205, which are deployed on both public and private establishments to minimize the possible outbreak of such virus/bacteria.

Furthermore, controlled irradiation system 110 of systems and methods herein are permanently directly hard wired into the power supply and without any readily available on/off power switch. Instead the switching mechanism is controlled by main keyed power switch 108, wherein main keyed power switch 108 can control or power a plurality of units of controlled irradiation system 110, which is under controlled access by a key, such that each unit within the plurality of units of controlled irradiation system 110 has power connected to them at all times. Typically, a unit of main keyed power switch 108 can be utilized for several units of controlled irradiation system 110 per one hall or room, wherein the unit of main keyed power switch 108 located inside this hall or room ("connected systems").

These connected systems in having power supplied to them (the keyed power switch 108 connecting the systems are in an "on" state) remains in this "standby" mode/state until main control center 201, such as the CDC, activates "on" or "off" states remotely. And only in an emergency such as construction, or unit maintenance and other emergency, a management entity can manually turn main keyed power switch 108 to an "off" state using their key. A management entity can immediately switch main keyed power switch 108 back to an "on" state (again using the key) whenever the emergency is over with and to keep these connected systems in the "standby" mode/state for the next remote turn an "on" state via a signal sent by main control center 201, such as the CDC.

While in this "standby" mode/state, electrical power through the keyed power switch 108 is connected to controlled irradiation system 110 containing UV-C lamps (lamps 101 and 102). Lamps 101 and/or lamps 102 can turn an "on" state via a signal sent by main control center 201, if controlled irradiation system 110 is within selected office hours. Upon receiving the turn "on" state signal, lamps 101 and 102 turn to (i.e., are within) an "on" state either: (1) continuously during the selected office hours; or (2) if after the selected office hours, only when activated by built-in motion sensor 104 for about 10 minutes or so per motion sensed activation and for each and every further subsequent motion sensed.

The UV-C lamps (lamps 101 and 102) of the connected systems under "standby" mode/state can be turned to an "off" state remotely by the CDC in instances such as: there is no perceived corona virus threat or any virus threat or no common flu threat. Lamps 101 and 1-2 can only be turned to an "on" state once main control center 201 determines that the threat warrants such action. This can be achieved by an algorithm applied by main control center 201 that allows the automatic transmitting of the signals for an "on" state, while there is still a COVID threat/virus threat, which could be several years; transmitting the signal for an "off" state when the CDC determines that there is no longer any threat; and wherein this transmission of signal for an "off" state is automatically repeated every hour for about 7 days.

Outside of these COVID related threats, and therefore, main control center 201 can send subsequent turn to "off" state signals. Main control center 201 can additionally send a "temporary turn on" state or a "temporary turn off" state signals to these systems for "Readiness Test" purpose or other reasons that main control center 201 deems fit.

While in "standby" mode/state, these connected systems, once remotely turned in an "on" state by the turn an "on" state signal sent by main control center 201, remain in an "on" state until main control center 201 turns the connected systems to an "off" state. The turning "on" state signal can be repeated every hour or so for redundancy purposes, while the threat or perceived threat exist, thereby: (1) ensuring that all the connected systems are in an "on" state and (2) if there are other units in the connected systems that may not have been turned to an "on" state the first time, ensuring that these units are in an "on" state in the next subsequent times. This subsequent turning to an "on" state by main control center 201 is especially targeted to those connected systems experiencing a power outage or even a tripped circuit breaker, which could have missed the first turning an "on" state signal from main control center 201 but should be turned to an "on" state by the subsequent turn to an "on" state signal from main control center 201, when the electrical power is restored. However, this next subsequent turning to an "on" state by main control center 201 can have no effect on those connected systems that are already turned to an "on" state. Note: the management/administrator entity of the facility or building within cluster 205 does not have final "say and/or control" (i.e., authorizations) over main control center 201 decision of turning an "on" state or an "off" state in these systems and methods herein. Stated another way, the non-transitory signals transmitted by main control center 201 are command center that can override entities at relay centers and the management/administrator entity of the facility or building within cluster 205, thereby the transmission of non-transitory signals by main control center 201 controls the authorization and thus operating states of the lamps within cluster 205. For example, the CDC, which is operating main control center 201, has the sole volition to this decision (i.e., control center volition), thereby eliminating any political aspect of whether the management agree/oppose such a CDC decision. Control center volition can be dictated by an algorithm, as implemented by main control center 201, wherein the algorithm is: (1) automating the assessment of lamp 101 and 102 performance; (2) deciding whether to activate "on", "off", or "standby" states; and (3) overriding the management entity in cluster 205.

Each unit of controlled irradiating center 110 further comprises: (1) infrared (IR) receiver 106 and (2) manual input port for programming the system used for entering data into the system's memory/CPU, such as the street number address of the facility (e.g., the address of a facility unit within cluster 205) that can have controlled irradiating center installed. The office hours and days of operation of the business or facility within cluster 205, the desired added length of time (~1 hour) before and after controlled irradiating center 110 can operate, which once activated, to supply power to the UVC lamps (lamps 101 and 102) and be processed by the CPU, thereby activating an "on" state of these lamps at the selected office hours and 1 hour or so before and after this selected added time (as per user's selection).

The entered street number of the physical address where this system is being installed, for example, if the location address is 1234 Wall Street, then 1234 can be entered/inputted in the system (either using the manual inputting or remotely using the handheld IR remote controller as the number of the street address. The input of "1234" determines the sequence of the actual elapsed time in seconds that controlled irradiating center 110 actually activates the "on" state of the UV-C Lamps (lamps 101 and 102) after receiving the turn "on" state signal from main control center 201, which in this case is 1,234 seconds after the first received turn "on" state signal from main control center 201. This sequencing of the actual turning an "on" state, after the first received main control center 201, turns an "on" state signal, which prevents the danger of causing an electrical load shock to the electrical supply system if all the system's UV-C Lamps can turn on at exactly the same time. Stated another way, if this sequencing is not in effectuated, overload of the power grid often occurs. Stated yet another way, the connected system, as instructed by main control center 201 instructs each unit of controlled irradiating center 110, to effectuate a sequence which keeps lamps 101 and/or lamps 102 in an "on" state for sufficient irradiation to remove pathogens; and systematically, yet in an automated fashion, keep lamps 101 and/or lamps 102 in an "off" state to reduce energy consumption and extend the life of the bulb in lamps 101 and 102. The inputted street address and this processed street address determine the sequenced exact time that the unit of controlling irradiation system 110 first turns to an "on" state or first turns to an "off" state. Note: the first turning to an "off" state is controlled by, or based on, the processed street address (i.e., processed by the street address by main control center 201). Therefore, the plurality of these installed units of lamps in controlled irradiation system 110 do not just turn to an "off" state at the same time, which can result in an electrical shock to the power grid (especially if there are millions of these installed nationwide). This is the same concept as the first initial turning to an "on" state in that the sequence is configure to protect the power grid from an electrical shock if all of these units turn on exactly at the same time. The sequence can be processed by master control center 201 with the aid of an IR receiver that receives IR signal from a controlling handheld remote controller (CHHRC) and an IR signal transmitter transmits an encoded IR signal comprising of the electronically stored data from a operationally connected memory, such as the previously inputted street address where the unit is physically installed at and the inputted time and day of the office hours of the establishment, whereby the unit transmits these inputted data from an operationally connected memory using an IR Transmitter whenever the unit receives an encoded "Report" code IR signal from the CHHRC having: (1) an electronic display panel that can display a viewer readable reading of the data received by an IR Receiver from the IAPED's IR Transmitter, whereby these received data by the CHHRC can be displayed on a display panel; and (2) an electronic display panel whereby the viewer readable displayed data on an electronic display panel comprising the street address and the designated operating office hours of the establishment/building/structure where the IAPED is physically installed.

By using this sequenced actual turning an "on" state, UV-C lamps (lamps 101 and 102) in any particular region (e.g., cluster 205) containing multiple facility units each equipped with one or more units of controlled irradiating center 110 can be turned to an "on" state at a sequenced time compared with the other system of a different street number address. For example, units of controlled irradiating center located in 1233 Wall Street turns to an "on" state on the 1,233 seconds after the first received signal from main control center 201, which is 1 second earlier than the system located at 1234 Wall Street address. However, all UV-C lamps from units of controlled irradiating center 110 located in an address having "1234" (i.e., 1234 Main St; 1234 Market St; 1234 Wall St; 1234 Broadway Blvd. etc.) can actually turn to an "on" state at the same time. For 222 Hoover St. address, the system's UV-C lamps can turn an "on" state on the "222" seconds after the first received turn to "on" state signal from main control center 201.

The CPU of controlled irradiating center 110 can use only the last four digits of the user's address. For example, if there are more than 4 digits in the address, only the last 4 digits are used; and if less than 4 digits—then all these digits can be used in the sequencing.

Moreover, before and after the selected office hours and the added time-controlled irradiating center 110 can revert to being motion activated, which means that all of the UV-C lamps can automatically turn to an "off" state unless there is a sensed motion by built-in motion sensor 104 by at least one unit of controlled irradiating center 110. This is designed to conserve power after the office hours, such that lamps 101 and/or 102 can come back to an "on" state if within the selected office hours (which includes the added 1 hour or so before and after these office hours). However, if there is motion sensed outside of these office hours, lamps 101 and/or 102 can turn to an "on" state for a pre-determined (and user selectable) length of time (~10 minutes or so), turn to an "off" state after this 10 minute or so time, and remain in an "off" state without any further subsequent motion sensed. If there are continuous motions sensed, controlled irradiating center 110 can remain on for an extended length of time even if outside of the selected office hours mode. This can be attributed by the possible overlapping of the ~10 minutes activation period per each motion sensed. On weekends, if selected as a "no office" day, controlled irradiating center 110 can operate under the outside of the selected office hours mode, whereby UV-C lamps (lamps 101 and 102) are turned to an "off" state unless there is motion sensed by motion sensors. For clarification, as an example, for a unit of controlled irradiating center 110 having a selected 9:00 A.M to 5:00 P.M. selected office hours Mondays-Fridays and having the selected added 1 hour, the UV-C lamps therein can: (1) automatically turn to an "on" state at 8:00 A.M. to 6:00 P.M.; and (2) automatically revert to being motion sensor activated from 6:01 P.M to 7:59 A.M. of the following morning. If this following morning falls on a selected weekend/no office days, then this UV-C lamp can remain in motion sensor activated status until the morning of the following Monday (being M-F workdays).

All these UV-C lamps turning to "on" and "off" states related to these office hours/workdays/street number, which turn first turn to an "on" state, are: (1) controlled by the system's memory/CPU; and (2) based on the user selected entry to this system's user programmable memory. Controlled irradiation system 110 can have a built in clock, which has a back-up power or similar to keep an accurate time/date even after a power outage.

The controlled irradiating center 110 can retain the last (i.e., most recent) turned "on" state or "off" state from main control center 201, even after a power outage. Being in "standby" mode/state, if main control center 201 sends a signal for an "off" state, the controlled irradiating center 110 can temporarily disable all respective UV-C lamps (unless under "Test" as explained above). If main control center 201 sends an "off" state signal and motion sensor 104 still functions, motion sensor 104 does not turn the UV-C lamps to an "on" state. Signals for an "off" state are sent by main control center 201, if main control center 201 determines that there are no longer any threat. Therefore, these UV-C lamps are no longer needed to conserve energy.

These units of controlled irradiating center 110 in an "off" state, as instructed by the signal from main control center 201, can remain in "standby" mode/state waiting for the next signal for an "on" state from main control center 201.

And for these features, these systems and methods herein are positioned to be one of the nation's permanent forefront defense against any threat or perceived threat of airborne pathogens including, but not limited to, corona virus, flu virus, chickenpox, and whooping cough. More particularly, controlled irradiating center 110 can easily, readily, and reliably be activated into an "on" state signal in an automated and sequential manner, as transmitted by the Main control center 201, which is controlled by the CDC (or any pertinent authorizing agency) should the need arise.

And just like the turn to the signal of an "on" state, main control center 201 transmits a turn to the signal of an "off" state, which can also repeat every hour or another time frame. For redundancy purposes, in the absence of these threats or perceived threats, this effectuated sequence can ensure that all units of controlled irradiating unit 110 within facility units of cluster 205, which are in telecommunication with main control center 201, are in an "off" state. If there are other units of controlled units 110 that are not turned to an "off" state by the first signal for an "off" transmitted/sent by main control center 201, then those units of controlled irradiation system 110 can be turned to an "off" state via subsequent "off" state signals sent by main control center 201. This subsequent turning "off" by main control center 201 is especially targeted to those units of controlled irradiation system 110 experiencing a power outage or even a tripped circuit breaker, which could have missed the first turning to an "off" state signal but should be turned to an "off" state by the subsequent turns to an "off" state signal, as transmitted by main control center 201, when the electrical power is restored.

However, this next subsequent turning to an "off" state signal, as sent by main control center 201 (i.e., the third "off" state signal), does not have an effect on those units of controlled irradiation system 110 that are already in an "off" state.

Controlled irradiation system 110 further comprises a built in infrared (IR) receiver 106 and IR transmitter 105. IR receiver 106 is configured for receiving input for programming features (address, office hours, etc., as described above) and is remotely controllable by the hand-held remote IR controller ("remote controller") of the user (if under "Program" mode). If the "Program" button is pushed momentarily while being pointed to a particular system, this "Program" mode allows the user to remotely modify the programmable features of this particular unit of controlled irradiation system 110, which is already installed overhead and in place (without having to take controlled irradiation system 110 down) within a facility unit of cluster 205.

Figure 4:
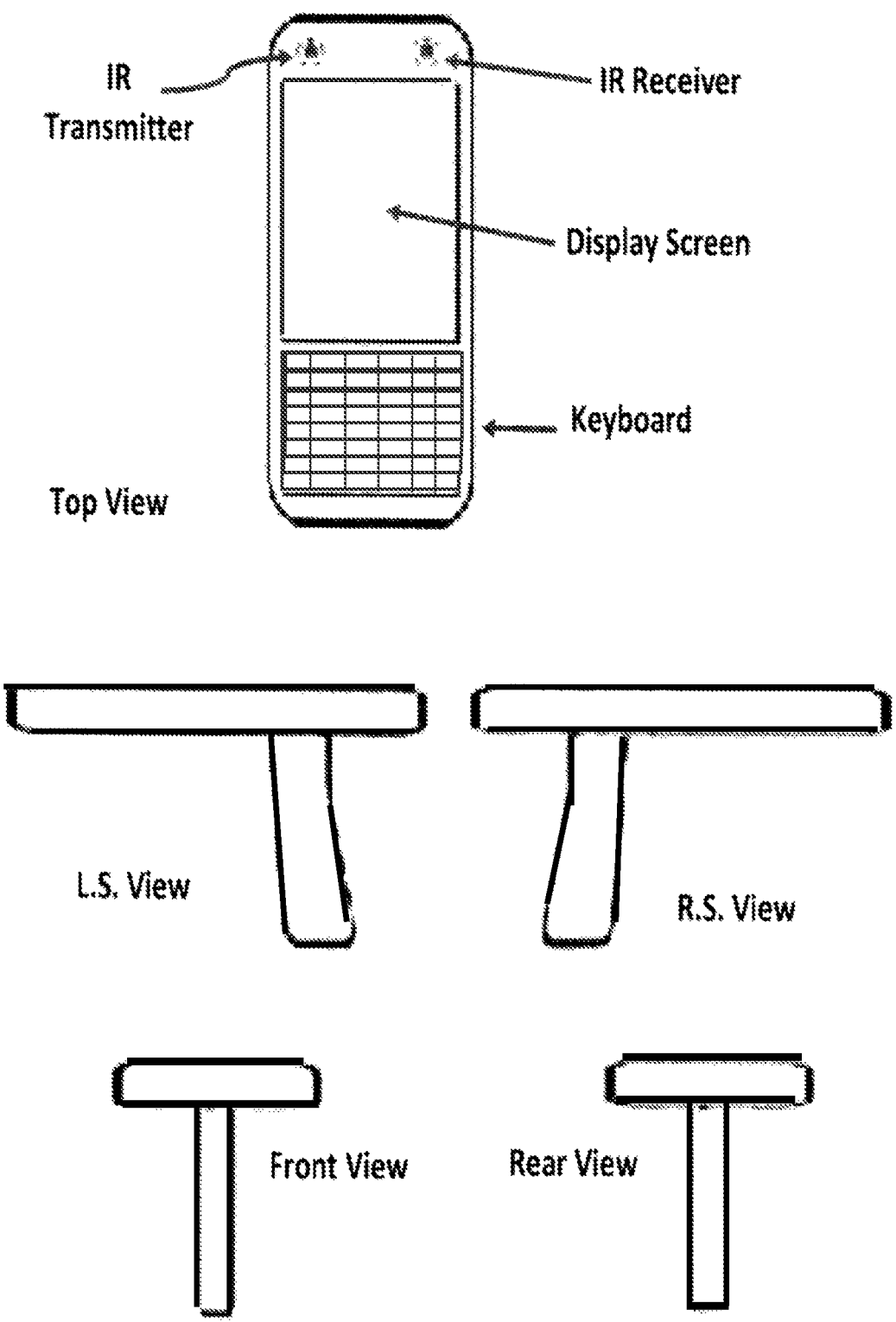
FIG. 4 is a block diagram of the control unit equipped with the IR transmitter and IR receiver; and lamps.
Figure 5:
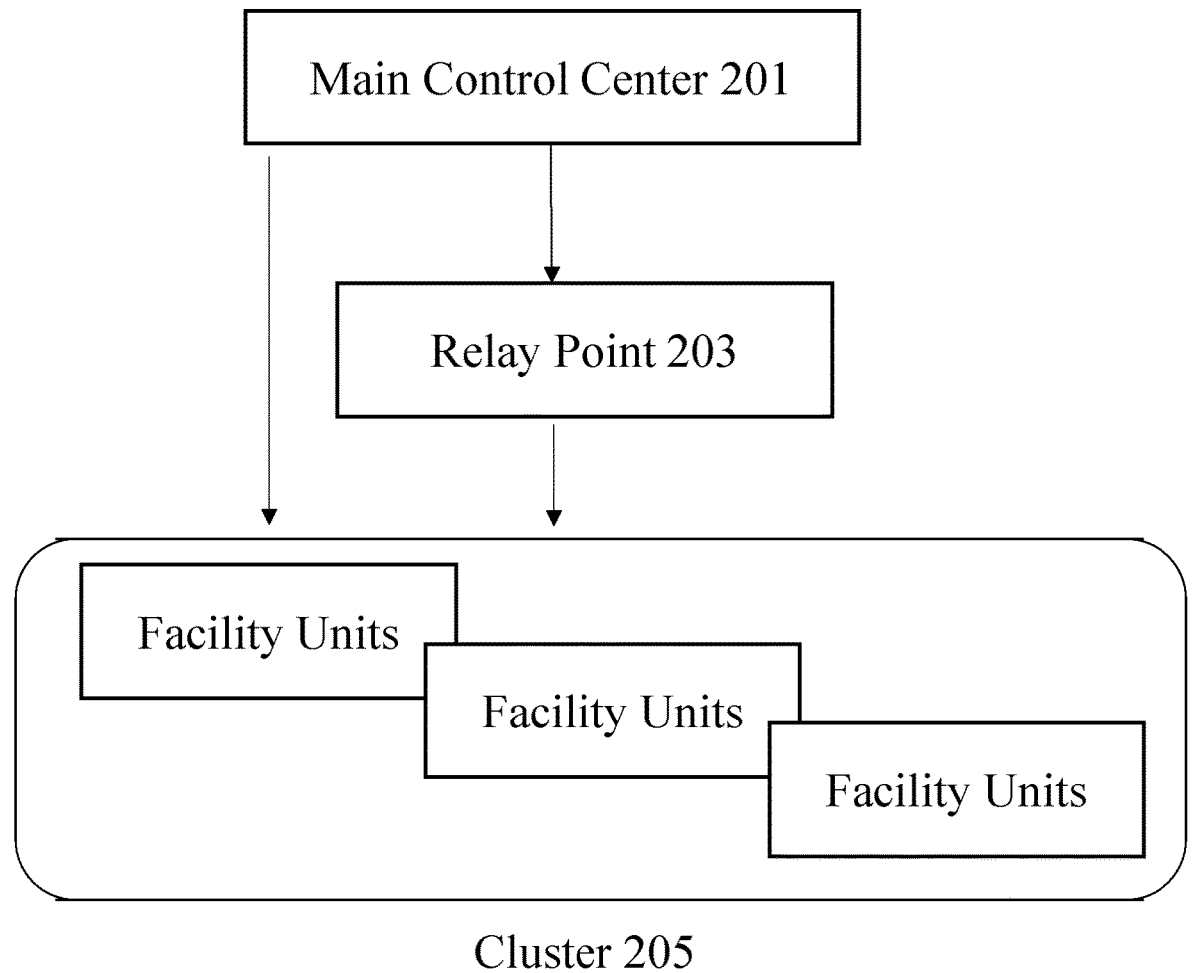
FIG. 5 is a block diagram of the telecommunication directions between the relay center, cluster containing facility units containing controlled irradiation systems, and main control center.

Moreover, if the "Report" button in FIG. 4 is pushed on the remote controller while pointed to this particular system, IR transmitter 105 is configured to transmit out the selected programmable features of this particular unit of controlled irradiation system 110 to the IR receiver 106 of the user's hand-held Remote Reader on a line of sight and in range, thereby allowing the user to remotely access and verify, which is being downloaded into the IR Receiver of the Remote Reader). The selected programmable features of this particular unit of controlled irradiation system 110 and the user having read from the Remote Reader, the CPU can process the selected programmable features to determine the selections that have been programmed in said particular unit of controlled irradiation system 110. If this user sees a need to amend or change the features, for example, due to change of building occupant which have a longer or even a 24 hour work hours, etc., under this "Report" mode, said particular unit of controlled irradiation system 110 continuously reports for about 1 minute and then stops reporting. The decoder in the Remote Reader can decode the received IR signal and convert this received signal to one readable by the user.

Furthermore, the user's remote controller in FIG. 4 has a third button as the "Test" button. When this "Test" button is pressed while pointed to a particular unit of controlled irradiation center 110, wherein said particular unit of controlled irradiation center 110 in standby mode/state can turn lamps 101 and/or 102 to an "on" state.

When "Test" button is pressed, lamps turn on for a brief period of about 1 minute, which is just enough time for the user to check if the UV-C lamp works using the hand-held Remote Reader. This Remote Reader has a built-in UV-C lamp sensor that can determine if the UV-C lamp(s) is/are working properly. Although, these UV-C lamps produce a visible light which determines if the UV-C lamps are working, the user can be safer if he or she does not look at the turned UV-C light directly when in an "on" state. Moreover, the Remote Reader can properly diagnose if the particular lamp has a diminished light output and would be subject for replacement.

Figure 2:
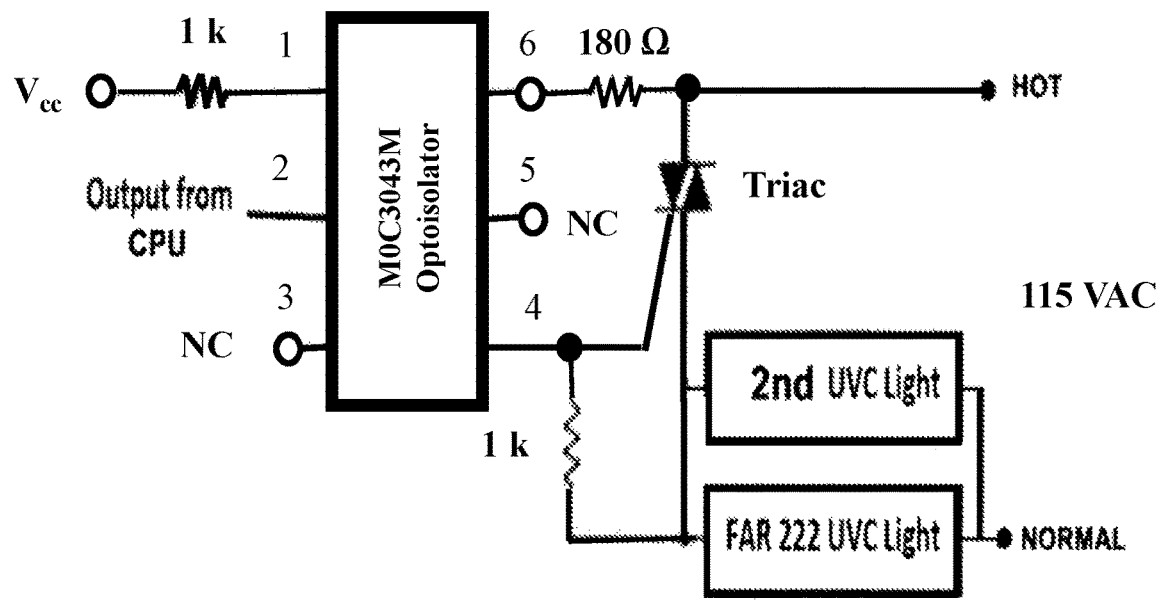

The circuit in FIG. 2 is the actual circuit represented in triac switch 107 in FIG. 1. The remote reader in FIG. 1, in conjunction with the IR Remote Controller in FIG. 4, can be used program the memory/CPU, like inputting the street address of the building where the UV-C lamp unit is installed; and to enter the designated office hour of the business where the UV-C lamp units are installed. However, the IR Remote Controller can control the circuit in FIG. 2, which is a switch controlled by master control center 201, as to the time the switch in FIG. 2 can be turned on during office hours. Additionally, if "TEST" button on the IR Remote Controller is pressed, the unit can: (1) immediately turn the "switch" in FIG. 2 to an "on" state associated with an "on" position for about 1 minute, to turn the UV-C lamp to an "on" state, for the maintenance person to test if the UV-C lamp is working; or (2) immediately turn the "switch" in FIG. 2 to an "off" state associated with an "off" position for about 1 minute, to turn the UV-C lamp to an "off" state, for the maintenance person to test if the UV-C lamp is responsive to signals from main control center 201.

Figure 3:
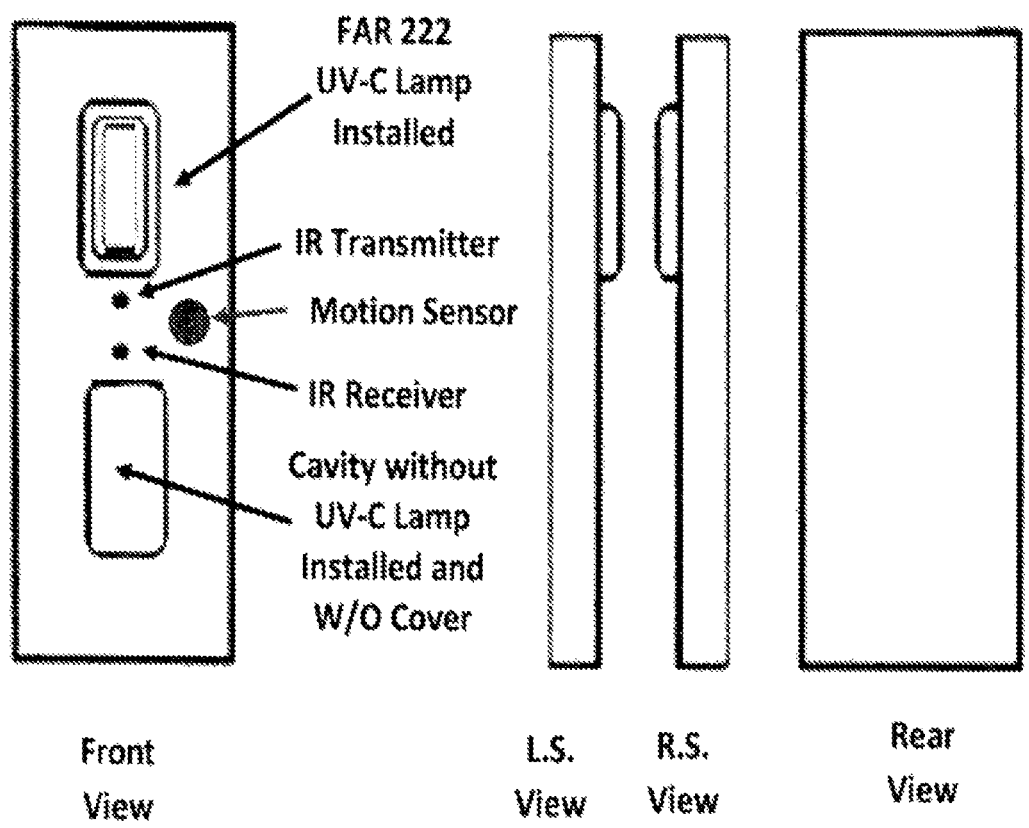
FIG. 3 is a block diagram of the lamp units and cavities.

FIG. 3 depicts the complete front, side, rear view of the individual unit of controlled irradiation center 110 that houses the two cavities, and one UV-C lamp installed in one of the two cavities; and FIG. 4 depicts an IR remote controller. More particularly, an individual unit of controlled irradiation center 110, which is installed overhead on the ceiling or hanging from the ceiling, can be operated by the hand-held IR remote controller in FIG. 4, which is in the hands of the maintenance person. This IR Remote Controller in the hand of the maintenance person can send directional infrared signal to the IR receiver on the individual unit of controlled irradiation center 110 overhead, thereby the IR receiver and controlled irradiation center 110 can communicate with each other.

FIG. 4 depicts the IR remote controller and the Remote Reader. In the preferred embodiment, the IR remote controller and the Remote Reader are combined in one hand-held unit for convenience.

In FIG. 3, controlled irradiation system 110 has a plug-in socket port to accept the second unit of UV-C lamp (i.e., lamp 102), wherein controlled irradiation system 110 has a built in electrical power storage means, such as a rechargeable battery and/or capacitor that stores power and supplies power to the system's clock and memory/CPU (but not the UV-C lamps). If there is a power outage, before controlled irradiation system 110 is physically installed and while electrical power is not yet available; this allows the user to manually program the selectable features in the memory before program controlled irradiation system 110 gets installed within a permanent placement location and before electrical power is connected to controlled irradiation system 110, using the user's portable computer/tablet. The unit has a USB port or the like that is hooked to the PC/Tablet's USB for this manual programming purpose.

According to the Jul. 14, 2021 issue of Healthcare: "There have been numerous studies published since the Covid-19 pandemic began pointing to the effectiveness of UV-C light in destroying the covid-19 virus. The most recent research was presented in this month at the British Association of Dermatologists' Annual Meeting, and was undertaken by NHS Tayside and the Universities of Dundee and St. Andrews" https://healthcareglobal.com/telehealth-and-covid-19/uvc-light-could-be-part-theatre-tech-against-covid-0. Moreover, it's been proven that this Care 222 which uses 222 nm far-UVC light sources is safe for use even in occupied spaces and poses minimum health risk to human skin or eyes compared with other non-222 nm UVC light sources. (Care222@ushio.com) And this is the very reason that using this Care 222 is preferred than the other UVC light source. In addition to having the Care 222 installed initially, this system has a vacant slot for one other UV or similar virus killing lamps. Controlled irradiation system 110 has the capability of having a maximum of two integral (2) UV-C lamps (lamps 101 and 102) or similar virus/bacteria killing lamps that may be installed on the system to combat the different virus variants in the future.

Moreover, controlled irradiation system 110 may be modified for airduct irradiation purpose to connect electrical power to a plurality (and not integrated into controlled irradiation system 110) of remote UV-C lamps, preferably the elongated bulb type lamps, and these lamps affixed transversely inside and in the middle portion of the airduct. These remote UV-C lamps operates similarly as with lamps 101 and 102, whereby if main control center 201, such as the CDC, sends an "on" state activation signal, these elongated bulb type lamps can turn on continuously during the designated office hours, and in this embodiment, an airduct airflow motion sensor activates the remote UV-C lamps after office hours. After office hours, if the air-conditioner or the heater is turned on, this produces an airflow inside the airduct, which can activate the airflow motion sensor in the airduct, which effectuate turning an "on" state of the remote UV-C lamps for about ~10 minutes for each activation. Continued airflow in the airduct caused by the continued after office hours operation of the air-conditioner or the heater, thereby resulting in the continued "on" state of the remote UV-C lamps in the airduct.

The controlled irradiation system 110 of system and methods herein is preferably installed overhead for maximum coverage for the overhead model embodiment; and preferably placed 10 feet apart on the ceiling or hanged overhead for an optimum distance of about 10-15 feet (even higher) from the floor. Additionally, controlled irradiation system 110 for the airduct model embodiment has a remotely wired elongated UV-C lamps preferably transversely installed in the middle portion of all airducts in the establishments to ensure that all air flowing out of the airducts has been irradiated.

In the systems and methods herein, a FAR UV-C Lamp system most preferably uses the filtered FAR UV-C Excimer Lamp Module used in Care 222® Filtered Krypton-Chloride 222 nm technology ("Care 222") manufactured by USHIO America. This particular Care 222 lamp produces light in a very safe and stable 222 nm range. This Care 222 has an added filtering which is proprietary to this lamp and is the key reason that it is preferred compared to the other UV-C type lamps that produces light outside at the 222 nm range.

This Care 222 lamp is fitted into the appropriate cavity somewhere in about the middle front side of the lamp housing with the output side facing out preferably as illustrated in FIG. 3. Certainly, the mere physical placement at or about the middle front side of the lamp housing is preferred among many other possible other places along the front surface of the housing. This housing although illustrated in FIG. 3 as rectangular, may be made in other shape such as oblong, square, circular, etc., as dictated by the manufacturer. The cavity allows lamps 101 and 102 to be fitted and positioned to maximize light emission, which in turn maximizes the eradication of pathogens.

Controlled irradiation system 110 has a second cavity that is designed to accommodate the second UV-C lamp or similar (i.e., lamp 102) as the need arise in the future. The two cavities (one for the first UV-C lamps and the second UV-C lamp) are designed for easy snap on fit, without the need to disassemble the unit from an installed placement location in the field. Lamps 101 and 102 have a connecting member, wherein the connecting member is curved, as depicted in the left side and right side views in FIG. 3, thereby allowing lamps to be fit securely into the cavities.

In FIG. 2, "hot" and "normal" are two alternating current power lines. This designates that the devices are directly connected to normal house power wall socket type. An optoisolator is a device that sends a triggering signal in a circuit without electrically connecting one to the other. For example, an "on" state signal (typically +5V) is produced by an output pin of an integrated circuit isolate this integrated circuit and allow this output to control the triac. For instance, this output from the integrated circuit is connected to the input of the opto-isolator, which oftentimes have a micro led bulb inside, and there is a sensor that senses this light to trigger the triac. Triac is a solid state power switch, thereby the built-in switch on turns to an "on" state electronically. And in an opto-isolator triac, by applying a very small signal to an input pin, can turn on the Triac power switch. This way, the Triac can turn on the power to the UV-C lamps, using only a very low power input triggering signal. The Triac does not reduce power consumption, by virtue of being only a "switch", that turns UV-C lamps in "on" and "off" states. However, the reduction in power consumption is during after office hours, when the individual units UV-C lamps does not continuously turn to an "on" state, and only turn to an "on" state for about 10 minutes every time the unit's motion detector senses body motion. If no body motion is sensed, the UV-C lamps are turned to an "off" state, and not consuming power. Thus, after office hours, the unit conserves power. However during the designated office hours, all the UV-C lamps are lit continuously, which consumes power.

The systems and methods herein comprises of the FAR 222 lamp connected in series with the Triac Control Switch, or any other power control switch, as illustrated in FIGS. 1 and 2. In FIG. 1, the designation of the two wires that carries current to supply electricity to lights and appliances to homes can be hot or neutral. The input pin 2 is connected to the output pin of the CPU in FIG. 1 and FIG. 2 (i.e., turning on an "on" state) sending an activation signal to pin 2 of the Triac Control Switch effectively turning the FAR 222 lamp to an "on" state, as well as the second UV-C lamp which may be added at a later stage. Pin 2 of MOC3043 Optoisolator Triac is the designated input pin. The application of a +5 VDC to this pin 2 of MOC3043 effectuates the turning to an "on" state of lamps 101 and 102. There is no other input pin in MOC3043, only pin 2. Pin 1 is not for input, but the pin to supply VDC+ voltage to this MOC3043.

The systems and methods herein in yet another embodiment that uses a third UV-C lamp, preferably an elongated UV-C lamp tube emitting omnidirectional UV-C light, instead of lamps 101 and 102 and third UV-C lamp is electrically wired in series with the triac control switch, similar to the connection arrangement of lamps 101 and 102 lamps (FIG. 1 and FIG. 2). Unlike lamps 101 and 102 which are integrated into controlled irradiation system 110, this third UV-C lamp is not integrated into housing of controlled irradiation system 110, and controlled irradiation system 110 serves only as the controller and remote power source of this third UV-C lamp. The preferred method of installation of this third UV-C lamp is through a formed access hole in the middle portion of the side panel of this airduct and positioned in such a way that this third UV-C lamp when turned on, shine light to the incoming air passing through this airduct to kill the harmful pathogens in the incoming air prior to circulation inside the establishments.

The systems and methods herein having the embodiment of the integrated UV-C lamps 101 and 102 intended for overhead installations are placed about 10 feet apart to effectively shine a directional lights downward to the occupants and the occupied spaces inside the establishment within cluster 205, while the systems and methods herein having the embodiment of the non-integrated third UV-C lamp is designed to shine omni-directional light to the incoming air flow inside the airduct within the establishment within cluster 205.

This handheld IR remote controller/reader in this system is a typical handheld home appliance IR remote controller type that sends out directional unique infrared signal to the IR receiver located on the front surface of the housing, as illustrated in FIG. 4. This handheld IR controller and reader can be universal components for use in the systems and methods herein. More specifically, the handheld IR controller and reader are the left side view, the right side view, the front view, and the rear view are depicted; and the top view shows the keyboard and display.

The system and methods herein further comprises a motion sensor (FIG. 1 and FIG. 4) positioned to sense any human motion within the range of the motion sensor, which when any such movement is sensed, in effect turn the UV-C lamps to an "on" state, when outside of the office hours (explained above). There is a 10 Minute Timer (Default but may be changed as per CDC guideline) activated the moment the motion sensor sense any human motion which in effect turns the UV-C lamps to an "on" state, during this 10 minutes.

The systems and methods herein having the embodiment using the non-integrated third UV-C lamp, in addition to having the human motion sensor, can have an additional external airflow sensor that senses the flow of incoming air inside the airduct, whereby, after the office hours, once this additional external airflow sensor sense airflow inside the airduct, the controlled non-integrated third UV-C lamp can be turned on for about 10 minutes per each sensed airflow, whereby the third UV-C lamp that is turned on after office hours. Similarly, these two embodiments; the one with the integrated lamps 101 and 102, and the non-integral third UV-C lamp remains in an "on" state continuously during office hours, and after these office hours are turned on by their corresponding motion sensors.

The systems and methods herein, the plurality of these unit of controlled irradiation system 110 can wirelessly/remotely make a periodic reporting of their status, cycle of events history, weekly testing history, etc. to a central remote monitoring station, such as Main control center 201, which enables this central remote monitoring station (CRMS) using the Digital Cellular Network (DCN) preferably 4G-LTE, 4G, 5G or any wireless data transmission means (WDT) in order to assess using AI of the CRMS each units' usage, maintenance/testing history, compliance and for the CRMS to contact the respective facility unit in cluster 205 and other pertinent authority for any violation and non-compliance.

Additionally, controlled irradiation system 110 can be electronically connected to an elongated UV-C lamp, wherein these elongated UV-C lamps are transversely installed inside of air ducting. Under this set-up, the FAR 222 UVC lamp (lamp 101) is not be installed on the controlled irradiation system 110 unit, but instead the unit can be used to power this external elongated UV-C lamp. This elongated UV-C lamp in this setup is not integrated into the unit but remotely wired; and several of these elongated UV-C lamp can be connected in parallel to just one controlled irradiation system 110, wherein controlled irradiation system 110 is controlled by main control center 201. In addition to the regular motion controller, controlled irradiation system 110 is connected to an external airflow motion sensor, that senses airflow inside the airduct, and once airflow is sensed, and during the outside of the office hours, the connected elongated UV-C bulb can be turned on for about ten minutes per sensed air flow. During office hours, this connected elongated UV-C bulb can continuously be turned on. Main control center 201 can implement continuous periodic transmission of signals to control the operating status of the lamps. For example, main control center 201 can: (1) transmit periodic signals associated with an "on" state, thereby activating the lamps within the housing system; and (2) transmit a subsequent signal associated with an "on" state, thereby maintaining the lamps within controlled irradiation system 110 in an "on" state, which can be spaced one hour apart.

Figure 6:
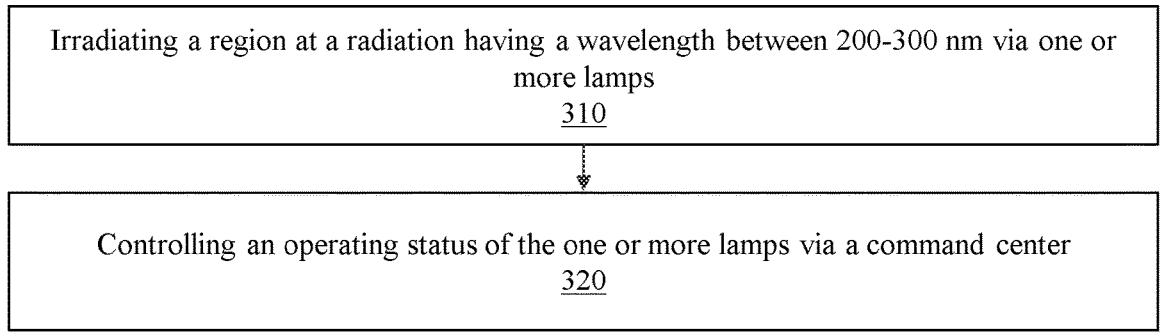
FIG. 6 and FIG. 7 are flowcharts illustrating a method for destroying pathogens, according to some embodiments of the present disclosure.
Figure 7:
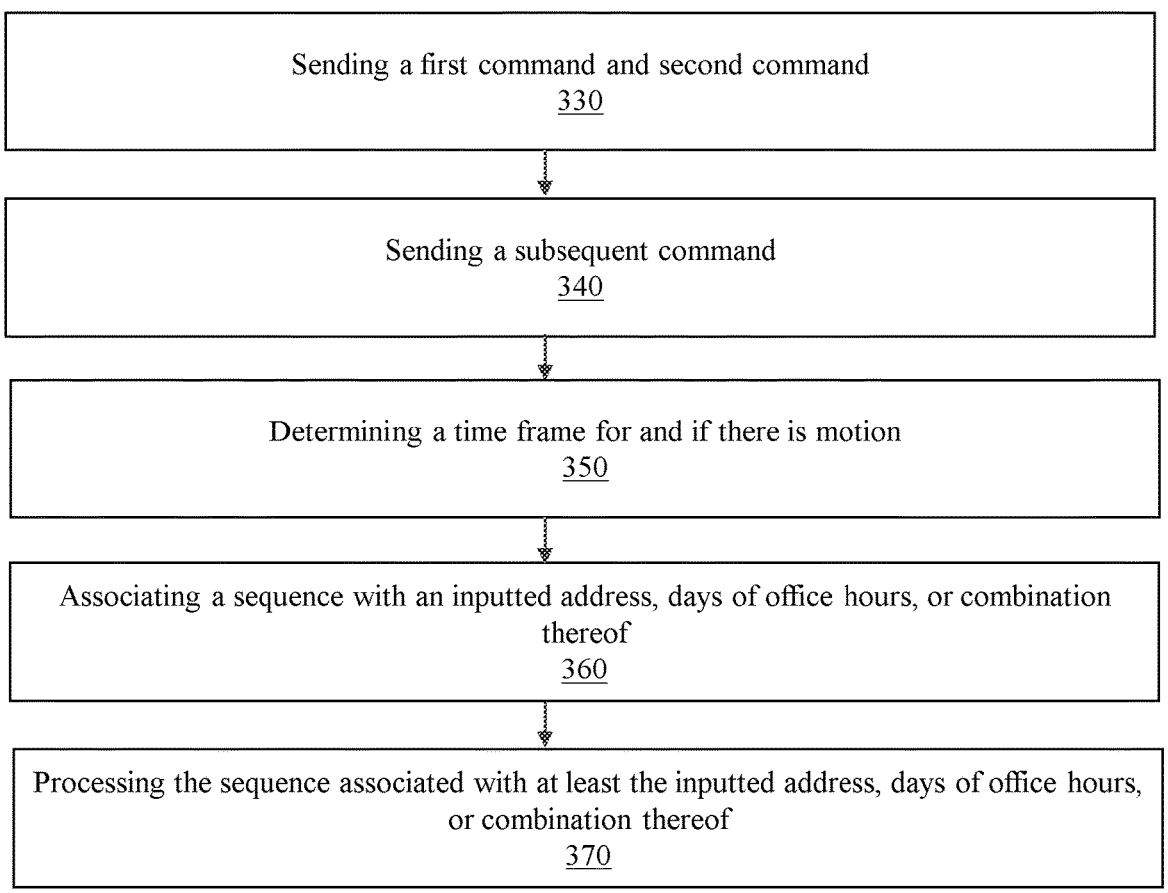

The flowchart in FIG. 6 that describes a method for destroying pathogens, according to some embodiments of the present disclosure. In some embodiments, at step 310, the method may include controlling an operating status of the one or more lamps (lamps 101 and 102) via a command center (main control 201). A step 320, the method may include irradiating a region at a radiation having a wavelength between 200-300 nm via one or more lamps operatively connected to a respective cavity. A control center, such as main control center 201, controls the operating status of at least one or more or all of the lamps in each of the units of controlled irradiation system 110 in the facility units if cluster 205 by the steps depicted in FIG. 7. At step 330, main control center 201, may include sending a first command and a second command. At step 340, main control center 201 may include sending a subsequent command for making further determinations and associations, as described with respect to steps 350 and 360. At step 350, main control center 201 may include determining a time frame of when the one or more lamps irradiate the region and if there is a motion. At step 360, main control center 201 may include associating a sequence with an inputted address, days of office hours, or combination thereof. At step 370, main control 201 may include processing the sequence associated with at least the inputted address, days of office hours, or combination thereof.

In some embodiments, the operating status may be a first state, a second state, or a third state. In some embodiments, the first state may be "on", the second state may be "off", and the third state may be "standby". In some embodiments, the first command and the second command may be an "on" state signal or an "off" state signal. In some embodiments, the first command may be an "off" state signal and the second command may be an "off" state signal, thereby putting each lamp in a second state.

In some embodiments, the first command may be an "on" state signal and the second command may be an "on" state signal, thereby putting each lamp in a first state. In some embodiments, the first command may be an "on" state signal and the second command may be an "off" state signal, thereby putting each lamp in a second state. In some embodiments, the first command may be an "off" state signal and the second command may be an "on" state signal, thereby putting each lamp in a first state.

In implementation of the various embodiments, embodiments of the invention may comprise a CPU (as described above) and a device for transmitting signals from main control center 201, such as a personal computing device (e.g., a personal computer), laptop, PDA, cellular phone or other personal computing or communication devices. A network computing device, such as a server or a plurality of servers, computers, or processors, combined to define a computer system or network, which uses a set of common communication protocols over digital interconnections for the purpose of sharing resources located on or provided by the network nodes, to provide the non-transitory signals.

The nodes of a computer system or nodes with in a network may include a bus or other communication mechanism for communicating information, which interconnects subsystems and components, such as a processing component (e.g., processor, micro-controller, digital signal processor (DSP), etc.), a system memory component (e.g., RAM), a static storage component (e.g., ROM), a disk drive component (e.g., magnetic or optical), a network interface component (e.g., modem or Ethernet card), a display component (e.g., CRT or LCD as a user interface), an external input component (e.g., keyboard or keypad), and/or cursor control component (e.g., mouse or trackball). A disk drive component may comprise a database having one or more disk drive components.

The computer system may perform specific operations by processor and executing one or more sequences of one or more instructions contained in a system memory component. Such instructions may be read into the system memory component from another computer readable medium, such as static storage component or disk drive component. Hardwired circuitry may be used in place of or in combination with software instructions to implement the invention.

Logic may be encoded in a computer readable and executable medium, which may refer to any medium that participates in providing instructions to the processor for execution. Such a medium may take many forms, including but not limited to, non-volatile media, volatile media, and transmission media. The computer readable medium is non-transitory (e.g., a non-transitory memory). In various implementations, non-volatile media includes optical or magnetic disks, such as disk drive component, volatile media includes dynamic memory, such as system memory component, and transmission media includes coaxial cables, copper wire, and fiber optics, including wires that comprise bus. In one example, transmission media may take the form of acoustic or light waves, such as those generated during radio wave and infrared data communications.

Some common forms of computer readable and executable media include, for example, floppy disk, flexible disk, hard disk, magnetic tape, any other magnetic medium, CD-ROM, any other optical medium, punch cards, paper tape, any other physical medium with patterns of holes, RAM, ROM, E2PROM, FLASH-EPROM, any other memory chip or cartridge, carrier wave, or any other medium from which a computer is adapted to read.

In various embodiments, execution of instruction sequences for practicing the invention may be performed by a computer system. In various other embodiments, a plurality of computer systems coupled by a communication link (e.g., LAN, WLAN, PSTN, or various other wired or wireless networks) may perform instruction sequences to practice the invention in coordination with one another.

Modules described herein can be embodied in one or more computer readable media or be in communication with one or more processors to execute or process the steps described herein.

A computer system may transmit and receive messages, data, information, and instructions, including one or more programs (i.e., application code) through a communication link and a communication interface. Received program code may be executed by a processor as received and/or stored in a disk drive component or some other non-volatile storage component for execution.

Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa (e.g., a virtual machine implementation or a logical hardware implementation).

Software, in accordance with the present disclosure, such as program code and/or data, may be stored on one or more computer readable and executable mediums. It is also contemplated that software identified herein may be implemented using one or more general purpose or specific purpose computers and/or computer systems, networked and/or otherwise. Where applicable, the ordering of various steps described herein may be changed, combined into composite steps, and/or separated into sub-steps to provide features described herein.

The foregoing disclosure is not intended to limit the present invention to the precise forms or particular fields of use disclosed. It is contemplated that various alternate embodiments and/or modifications to the present invention, whether explicitly described or implied herein, are possible in light of the disclosure. Having thus described various example embodiments of the disclosure, persons of ordinary skill in the art can recognize that changes may be made in form and detail without departing from the scope of the invention. Thus, the invention is limited only by the claims.

What is claimed is:

1. A method for destroying pathogens comprising:
universally wirelessly, simultaneously, and indiscriminately controlling an operating status of each pathogen lamp of a plurality of pathogen lamps installed within a respective cavity of a housing system of one or more housing systems, inside each participating establishments, facilities, buildings throughout the vast geographical region of a country within a cluster, by transmitting one or more non-transitory signals from a control center that simultaneously control the plurality of pathogen lamps in the cluster by:
sending a first command;
sending a second command; and
sending a subsequent command after the first command and the second command for determining a time frame of when one or more pathogen lamp of the plurality of pathogen lamps irradiate the region;
determining if there is a motion; and processing a sequence associated with (i) an inputted address, (ii) days of office hours, or (iii) the inputted address and the days of office hours; and
irradiating one or more regions within the cluster at a radiation having a wavelength between 200-300 nm via the one or more pathogen lamps of the plurality of lamp units operatively connected to a respective cavity, in response to transmitting at least one or more of the non-transitory signals as a command signal for controlling the operating status, based on the processed sequence associated with the inputted address, the days of office hours, or the input address and the days of the office hours, and if the motion is determined.

2. The method of claim 1, wherein the operating status is a first state, a second state, or a third state.

3. The method of claim 2, wherein the first state is on, the second state is off, and the third state is standby.

4. The method of claim 1, wherein the first command and the second command is an on signal or an off signal.

5. The method of claim 4, wherein the first command is an off signal and the second command is an off signal, thereby putting each pathogen lamp of the plurality of pathogen lamps in a second state.

6. The method of claim 4, wherein the first command is an on signal and the second command is an on signal, thereby putting each pathogen lamp of the plurality of pathogen lamps in a first state.

7. The method of claim 4, wherein the first command is an on signal and the second command is an off signal, thereby putting each pathogen lamp of the plurality of pathogen lamps in a second state.

8. The method of claim 4, wherein the first command is an off signal and the second command is an on signal, thereby putting each pathogen lamp of the plurality of pathogen lamps in a first state.

9. The method of claim 1, further comprising an algorithm, as implemented by the control center, wherein the algorithm is: (1) automating an assessment of performance of each pathogen lamp of the plurality of pathogen lamps by (2) deciding whether to activate a first state, second state, or a third state, wherein the control center overrides a management entity in the cluster.

10. The method of claim 1, further comprising using motion detectors to determine the operating status of each pathogen lamp of the plurality of pathogen lamps.

11. The method of claim 1, further comprising transmitting periodic non-transitory signals associated with a first state, thereby activating each pathogen lamp of the plurality of pathogen lamps within the one or more housing systems, and transmitting a subsequent non-transitory signal associated with a first state from the command center.

12. The method of claim 11, wherein transmitting the subsequent non-transitory signal associated with the first state is spaced at one hour apart.

13. The method of claim 1, wherein transmitting the one or more non-transitory signals further comprises transmitting the one or more non-transitory signals from the control center to a relay center, wherein the relay center processes the one or more non-transitory signals for transmission to the one or more housing systems, thereby controlling the operating status of each pathogen lamp of the plurality of pathogen lamps.

14. The method of claim 1, further comprises a relay center, wherein the relay center determines if each housing system of the one or more housing systems is in a fourth state or a fifth state to apply a policy over the one or more housing systems.

15. The method of claim 1, wherein the fourth state is associated with an operationally compliant status and the fifth state is associated with an operationally non-compliant status.

16. A computer system for destroying pathogens, comprising:
a command center telecommunicatively connected with one or more housing systems within a cluster;
a plurality of pathogen lamps operatively connected within the one or more housing systems, wherein each housing system of the one or more housing systems contains one or two cavities, wherein the one or two cavities are configured to receive a respective pathogen lamp unit of the plurality of pathogen lamps;
wherein the command center transmits one or more non-transitory signals from a control center that simultaneously control the plurality of pathogen lamp in the cluster for:
sending a first command;

sending a second command;

sending a subsequent command after the first command and the second command for determining a time frame of when the one or more lamps irradiate the region;

determining if there is a motion; and processing a sequence associated with (i) an inputted address, (ii) days of office hours, or (iii) the inputted address and the days of office hours; and irradiating one or more regions within the cluster at a radiation having a wavelength between 200-300 nm via one or more pathogen lamps of the plurality of pathogen lamps operatively connected to a respective cavity, in response to transmitting at least one or more of the non-transitory signals as a command signal for controlling the operating status, based on the processed sequence associated with the inputted address, the days of office hours, or the input address and the days of the office hours and if the motion is determined.

17. The computer system of claim 16, further comprises a relay center, wherein the relay center is operatively connected to the command center and the one or more housing systems within the cluster.

18. The computer system of claim 17, further comprising determining if each housing system of the one or more housing systems is in an operationally compliant status or an operationally non-compliant status to apply a policy over the one or more housing systems.

19. The computer system of claim 16, wherein the operating status is a first state, a second state, or a third state.

20. The computer system of claim 19, wherein the first state is on, the second state is off, and the third state is standby.

* * * * *